US012678542B2

(12) United States Patent
Gong et al.

(10) Patent No.: US 12,678,542 B2
(45) Date of Patent: *Jul. 14, 2026

(54) POLYETHYLENIMINE COPOLYMER COMPOSITIONS AND METHODS TO ENHANCE ANTIVIRAL AND ANTIBACTERIAL PROPERTIES OF MEDICAL DEVICES AND MEDICAL TOOLS

(71) Applicant: C-POLAR Technologies, Inc., Las Vegas, NV (US)

(72) Inventors: Jianliang Gong, Hong Kong (HK); Chun Yin Or, North Vancouver (CA)

( * ) Notice: Subject to any disclaimer, the term of this patent is extended or adjusted under 35 U.S.C. 154(b) by 218 days.

This patent is subject to a terminal disclaimer.

(21) Appl. No.: 18/409,776

(22) Filed: Jan. 10, 2024

(65) Prior Publication Data

US 2024/0226388 A1     Jul. 11, 2024

Related U.S. Application Data

(60) Provisional application No. 63/438,386, filed on Jan. 11, 2023.

(51) Int. Cl.
| | |
|---|---|
| *A61L 29/16* | (2006.01) |
| *A61L 29/04* | (2006.01) |
| *A61L 29/08* | (2006.01) |

(52) U.S. Cl.
CPC ............. *A61L 29/16* (2013.01); *A61L 29/049* (2013.01); *A61L 29/085* (2013.01); *A61L 2300/408* (2013.01)

(58) Field of Classification Search
CPC ................................ A61L 29/16; A61L 29/049
See application file for complete search history.

(56) References Cited

U.S. PATENT DOCUMENTS

| | | | |
|---|---|---|---|
| 4,039,440 | A | 8/1977 | Cadotte |
| 10,087,405 | B2 | 10/2018 | Swanson et al. |
| 10,577,570 | B2 | 3/2020 | Miracle et al. |
| 2009/0299259 | A1 | 12/2009 | Nguyen et al. |
| 2010/0136072 | A1 | 6/2010 | Haldar et al. |
| 2011/0059146 | A1 | 3/2011 | Lee |
| 2020/0221694 | A1 | 7/2020 | Purschwitz et al. |
| 2023/0097006 | A1 | 3/2023 | Gong et al. |

FOREIGN PATENT DOCUMENTS

| | | |
|---|---|---|
| CN | 101501269 A | 8/2009 |
| CN | 103952907 A | 7/2014 |
| CN | 105040240 A | 11/2015 |
| CN | 106948088 A | 7/2017 |
| CN | 106731229 B | 1/2019 |
| CN | 109310936 A | 2/2019 |
| CN | 208490931 U | 2/2019 |
| CN | 109862798 A | 6/2019 |
| CN | 109289327 B | 5/2020 |
| CN | 112606509 A | 4/2021 |
| JP | H11319441 A | 11/1999 |
| JP | 4517247 B1 | 8/2010 |
| KR | 10179556 B1 | 11/2017 |
| KR | 102033119 B1 | 10/2019 |
| KR | 20220014206 A | 7/2020 |
| WO | WO2010027539 A1 | 3/2010 |
| WO | WO2012049250 A2 | 4/2012 |
| WO | WO20191956 A1 | 10/2019 |
| WO | WO2021257279 A1 | 12/2021 |

OTHER PUBLICATIONS

Jung et al., "Surface Energy of Filtration Media Influencing the Filtration Performance against Solid Particles, Oily Aerosol, and Bacterial Aerosol," Polymers, 2019, 11, 935-948, MDPI, Basel, Switzerland.
Luo et al., "A Cleanable Self-Assembled Nano-SiO2/PTFE/PEI)n/ PPS Composite Filter Medium for High-Efficiency Fine Particulate Filtration," Materials, 2021, 14, 7853-7869, MDPI, Basel, Switzerland.
Fine et al., "Self-Charging Textile Woven from Dissimilar Household for Air Filtration: A Proof of Concept," ACS Omega, 2021, 6, 26311-26317, ACS Publications, Washington, DC.
Wang et al., "Deep Removal of SO2 from Cathode Air over Polyethylenimine-Modified SBA-15 Sorbents for Fuel Cells," Catalysis Today, 371, 240-246, Elsevier, Amsterdam, Netherlands.
Beselga et al., "Silver Nanoparticles—Polyethyleneimine-Based Coatings with Antiviral Activity against SARS-COV-2: A New Method to Functionalize Filtration Media," Materials, 2022, 15, 4742-4757, MDPI, Basel, Switzerland.
Wang et al., "Triboelectric charging of melt-blown nonwoven filters with high filtration efficiency," Scientific Reports, 2022, 12, 1146-1154, Springer Nature, New York.
Bourahla et al., "Grafting of Amine Functions on Cellulose Acetate Fibers by Branched Polyethylenimine Coating," Reactive and Functional Polymers, 2022, 170, 105107-105155, Elsevier, Amsterdam, Netherlands.
Wiegand et al., "Comparative in vitro study on cytotoxicity, antimicrobial activity, and binding capacity for pathophysiological factors in chronic wounds of alginate and silver-containing alginate," Wound Repair and Regeneration, 2009, 17(4), 511-521, Wiley, Hoboken, NJ.
Qiu et al., "Antimicrobial membrane surfaces via efficient polyethyleneimine immobilization and cationization," Applied Surface Science, 2017, 426, 972-979, Elsevier, Amsterdam, Netherlands.

*Primary Examiner* — Andrew S Rosenthal
*Assistant Examiner* — Danielle Kim

(57) ABSTRACT

The present invention offers compositions and methods of infusing antibacterial and antiviral polyethylenimine compounds into materials conventionally used for medical devices and medical tools, including such materials as vinyl, polyvinylchloride, latex, rubber, silicone and plastic materials, and thereby enhancing the safety and antiviral properties of such medical equipment.

16 Claims, 1 Drawing Sheet

POLYETHYLENIMINE COPOLYMER COMPOSITIONS AND METHODS TO ENHANCE ANTIVIRAL AND ANTIBACTERIAL PROPERTIES OF MEDICAL DEVICES AND MEDICAL TOOLS

CROSS-REFERENCE TO RELATED APPLICATIONS

The present application is related to U.S. Provisional Patent Application No. 63/438,386, filed on Jan. 11, 2023, which is hereby incorporated in its entirety.

FIELD OF THE INVENTION

The present disclosure relates to the field of imbedding antibacterial and antiviral polyethylenimine compounds into conventional materials used for medical devices, including such materials as vinyl, polyvinylchloride, latex, rubber, silicone and plastic materials.

BACKGROUND OF THE INVENTION

The current pandemic and the persistent issue of nosocomial infections and iatrogenic medical conditions draws clear attention and emphasis to the need for adding and enhancing antiviral and antibacterial properties of what should already be "sterile" medical tools and devices, including catheters, syringes, and similar common medical implements. As recent research has shown, a significant majority of nosocomial, or hospital-acquired, urinary tract infections are initiated by urinary catheters, which are commonly used in the general population of hospitalized patients. Notably, the annual costs of treating urinary tract infections in the United States are in excess of $451 million. The need to mitigate and defray such exorbitant and unnecessary medical expenses illustrates the profound promise of medical innovations that can address this problem.

SUMMARY OF THE INVENTION

The present disclosure offers compositions and methods of adding and infusing polyethylenimine solutions into medical tool base compositions, including the addition of polyethylenimine into vinyl and polyvinyl chloride catheters and medical tubing to add and enhance the safety and sterility of such medical tools and devices, and to reduce the incidence and severity of nosocomial infection, including, for example, urinary tract infections among the medical patient population.

The present invention offers a new copolymer between polyethylenimine and silicone. Rather than a polyethylenimine surface coating on a silicone base, this copolymer material presents a significantly higher durability and usefulness than the surface coating, particularly as the presence of the copolymer throughout the material means that the antiviral-effective properties do not fragment away, slough or "shed" as an antiviral agent applied strictly as a coating or surface application on an underlying base material is prone to.

The present invention is equally useful and effective across various common medical equipment materials, including latex, silicone, vinyl and polyvinyl chloride.

BRIEF DESCRIPTION OF THE DRAWINGS

FIG. 1 shows the chemical structure of (linear) polyethylenimine along with an expanded representation of the structure of linear polyethylenimine.

FIG. 2 shows an exemplar representation of branched polyethylenimine.

DETAILED DESCRIPTION OF THE INVENTION

The present application is described in detail below in conjunction with figures and specific embodiments to enable a person of ordinary skill in the art to make and use the various embodiments. Descriptions of specific devices, techniques, and applications are provided as examples. Various modifications to the examples described herein will be readily apparent to those of ordinary skill in the art, and the general principles defined herein may be applied to other examples and applications without departing from the spirit and scope of the present invention. Thus, the disclosed invention is not intended to be limited to the examples described herein and is to be accorded the full breadth and scope consistent with the claims.

In the present invention, polyethylenimine, as depicted in linear form in FIG. 1, and, alternatively, as depicted in branched polyethylenimine form in FIG. 2, is blended with silane and chitosan in effective concentrations, which produces a surface charge that can be substantially 3× stronger than existing formulations. The resultant material is readily adapted for fabrication and use as tubes, plates and gels. The materials of the invention demonstrate effective antiviral and antibacterial activity and thus offer great potential antiinfection use in medical devices and tools, including catheters, implantable devices, and tubing.

In a preferred embodiment of the compositions and methods of the present invention, 14.72 g E41 silicone is mixed with 1.28 g polyethylenimine (8% of silicone mass) on a silicone gel plate. In other preferred embodiments, the amount of polyethylenimine ranges between substantially about 2% to substantially about 10% of the silicone mass. The mixture is rested for 27 hours. Subsequently, the mixture (with the silicone gel plate) is conditioned in an oven at temperatures under 60° C. for 12 hours, resulting in form polymerization and cross-linking.

Continuing with the preferred embodiment methods of the present invention, the silicone gel plate is extricated and removed from the mixture. The mixture is then rested at room temperature conditions for 7 days.

In the preferred method of the present invention, following the 7-day rest, the mixture is submerged in 400 ml deionized water for 24 h to reach dynamic equilibrium between polyethylenimine and silicone. Finally, the mixture is conditioned in an oven at a temperature under 60° C. for 1 hour to extract water from the silicone.

In preferred embodiments of the invention, by submerging the novel polyethylenimine-silicone copolymer overnight under stable and steady conditions, rather than washing silicone via ultrasonic methods, the polyethylenimine redistributes throughout the silicone material, achieving a dynamic equilibrium between the water solution and the silicone material. Upon achieving dynamic equilibrium, the copolymer can produce non-cytotoxic material with strong antimicrobial and antiviral properties.

In preferred embodiments of the invention, the positive polarity across the polyethylenimine/silicone copolymer surface promotes an effective reduction of blood coagulation, as the positive polarity repels iron in blood.

In the present invention, the copolymerization of silicone with polyethylenimine does not impact or reduce the physical functionality of the silicone materials, as the concentration of polyethylenimine is low enough to promote beneficial therapeutic functionality while also avoiding deleterious effects on the physical, functional properties of the silicone materials themselves.

The effective concentration for obtaining good antimicrobial activity via the structures and methods of the present invention comprises a narrow range. This narrow effective range also encompasses other beneficial characteristics, including (low) cytotoxicity, effectiveness against the clotting of blood volume, and retention of the range of expected and desired physical characteristics of the medical equipment itself.

The copolymer compositions of the present invention can be used in myriad medical, dental, and other commercial applications; preferred embodiments of the present invention include use in catheters, including but not limited to vascular catheters, cardiovascular catheters, pulmonary artery catheters, central venous catheters, intraventricular shunts, peripheral venous catheters, urinary catheters, peritoneal catheters, epidural catheters, central nervous system catheters; medical tubing, e.g., breathing tubes, tracheostomy tubes, endotracheal tubes, nasogastric tubes, endotracheal tubes, percutaneous gastric tubes, percutaneous jejunostomy tubes, nasojejunal tubes, nephrostomy tubes; medical-grade electrodes, clips, fasteners, containers, syringes, hoses, CPAP machine hoses, CPAP face masks, asthma hoses, respirators, biofilms and biofilaments.

Further, as indicated, the methods and compositions of the present invention are not limited to catheters, tubing, or syringes, and may be incorporated in the production, fabrication and use of related medical tools, goods, and equipment, including blood exchange devices, implantable devices, such as stents, biliary stents, arterial lines, pacemakers, shunts, ports, vascular access ports, infusion and injection ports, wiring, extracorporeal circuits, implantable prosthetics, dental implants, mammary implants, penile implants, marital aids, condoms, tendons, cranio/facial tendons, ligaments, menisci, disks, rods, artificial voice boxes, artificial bones, artificial joints, artificial organs, pumps, heart valves, vascular grafts, scopes, including scopes used for endoscopy or laparoscopy procedures, and bandages, patches, and sutures, including cardiovascular sutures, with equally beneficial results and functionality. The methods and compositions of the present invention may also be used with the same beneficial properties, including antiviral efficacy, and functionality in ancillary uses and products, including, for example, in non-medical tubing, clips, fasteners, containers, food storage containers, cell phone cases, non-medical respirators, scuba or other diving or aviation breathing facemasks, hoses, and equipment, syringes, hoses, paints, dry wall/sheetrock, false ceilings and other building materials, structures, and fabrics.

While various embodiments of the invention have been described, it will be apparent to those of ordinary skill in the art that many more embodiments and implementations are possible that are within the scope of the invention. In addition, the various features, elements, and embodiments described herein may be claimed or combined in any combination or arrangement.

What is claimed is:
1. An antiviral medical device material, comprising:
    a cationic polymeric space-charge electret material with antiviral properties bonded to a medical device material, wherein the cationic polymer is natural, semi-synthetic, or synthetic;

further wherein the cationic polymer has a linear, branched, hyper-branched or dendrimer-like structure and the cationic polymer comprises at least cationic bearing group located in the backbone or side chain of the cationic polymer; and
    wherein the medical device material is vinyl, polyvinyl-chloride, latex, rubber, silicone, or plastic.
2. The antiviral medical device material of claim 1, wherein the cationic polymer is selected from the group of PEI, linear polyethylenimine, branched polyethylenimine, gelatin, chitosan, cationic peptides, cationic cyclodextrin, cationic dextran, cationic cellulose, polylysine, polyamidonamine, poly(amino-co-ester)s, or poly[2-(N,N-dimethyl-amino) ethyl methacrylate] polyethylenimine.
3. The antiviral medical material of claim 2, wherein the cationic polymer is polyethylenimine.
4. The antiviral medical material of claim 3, wherein the space charge electret material comprises 0.195%-10% by weight polyethylenimine cationic polymer.
5. The antiviral medical device material of claim 4, wherein the space-charge electret material comprises substantially 2%-8% by weight polyethylenimine cationic polymer.
6. The antiviral device material of claim 1, wherein the material has a substantially uniform surface charge with a minimum average positive surface charge of 2-35 nC cm$^{-2}$.
7. The antiviral medical device material of claim 1, wherein the material retains antiviral efficacy upon weaving, bonding, blending or mixture in a volume with other, non-antiviral materials.
8. The antiviral device material of claim 1, wherein the material is formed as a flexible hollow tubular structure.
9. A method of manufacturing an antiviral medical device material, comprising:
    dissolving a space-charge electret material in a suitable solvent to form a space-charge electret material/solvent mixture, wherein the concentration of the space-charge electret material in the solvent is 0.195%-10% by weight;
    mixing the space-charge electret with silicone material on a silicone gel plate;
    resting the mixture for 0-24 hours; conditioning the mixture for 0-24 hours at temperatures under 60 C; then extricating and removing the silicone gel plate, resulting in antiviral medical device material.
10. The method of claim 9, wherein the space-charge electret material is dissolved in a solvent with no added salt.
11. The method of claim 10, wherein the solvent is water.
12. The method of claim 10, wherein the solvent is methanol.
13. The method of claim 9, wherein the space-charge electret material is 0.195%-10% by weight polyethylenimine.
14. The method of claim 13, wherein the space-charge electret material is substantially 2%-8% by weight polyethylenimine.
15. The method of claim 9, wherein the resultant antiviral medical material has a substantially uniform surface charge with a minimum average positive surface charge of 2-35 nC cm$^{-2}$.
16. The method of claim 15, wherein the antiviral medical material is formed as a flexible hollow silicone tube.

* * * * *